US00PP12685P2

(12) United States Plant Patent
Bak et al.

(10) Patent No.: US PP12,685 P2
(45) Date of Patent: Jun. 11, 2002

(54) AECHMEA PLANT NAMED 'PRIMERA'

(75) Inventors: Elly Bak, Rijsenhout; Nicolaas D. M. Steur, Oude Niedorp, both of (NL)

(73) Assignee: Corn. Bak B.V., Assendelft (NL)

( * ) Notice: Subject to any disclaimer, the term of this patent is extended or adjusted under 35 U.S.C. 154(b) by 0 days.

(21) Appl. No.: 09/244,097

(22) Filed: Feb. 4, 1999

(51) Int. Cl.[7] ..... A01H 5/00

(52) U.S. Cl. ..... Plt./370

(58) Field of Search ..... Plt./370

(56) References Cited

FOREIGN PATENT DOCUMENTS

| | | |
|---|---|---|
| EP | 98/1095 A1 | 8/1998 |
| EP | 98/1095 A2 | 6/1999 |

OTHER PUBLICATIONS

GTITM UPOVROM citation for 'Primera' as per NL PBR BRM0055; Apr. 20, 1995.*

* cited by examiner

*Primary Examiner*—Bruce R. Campell
*Assistant Examiner*—Michelle Kizilkaya
(74) *Attorney, Agent, or Firm*—Foley & Lardner

(57) ABSTRACT

A new cultivar of *Aechmea fasciata* named 'Primera' characterized by its primary bract color of RHS 66D; broadly obovate leaves which are spineless with a dark greyed-green color (RHS 189A) and transverse white bands and patches.

1 Drawing Sheet

The present invention relates to a new and distinct cultivar of *Aechmea fasciata*, a genus within the family of Bromeliaceae, hereinafter referred to by the cultivar name 'Primera'.

BACKGROUND OF THE INVENTION

Aechmea comprises a genus of more than 168 species of evergreen perennials suitable for cultivation in the home or in the greenhouse. Aechmea may be terrestrial or epiphytic. For the most part, the species vary in diameter from 12 to 18 inches to 3 or 4 feet and have rosettes of spiny-edged leaves.

Flowers and bracts of Aechmea frequently have brilliant colors and may last for several months. The range of colors for Aechmea is generally from the yellow through orange but may also include pink, orange, red and red-purple. Tubular, three-petalled flowers may also appear but are usually short-lived.

Aechmea may be advantageously grown as pot plants for greenhouse or home use. Typically, the plants are shaded from direct sunlight; and the central, vaselike part of the leaf rosette is normally filled with water.

Aechmea is native to tropical America. Leaves of the Aechmea are usually formed as basal rosettes which are still and entire and in several vertical ranks. Aechmea has terminal spikes or panicles which are often bracted with petals united in a tube longer than the calyx.

Asexual propagation of Aechmea is frequently done through the use of tissue culture practices. Propagation can also be from offshoots which can be detached from the mother plant and grown in an appropriate soil or bark mixture. Methods for cultivating and crossing of Aechmea are well known. For a detailed description, reference is made to the following publications, the disclosures of which are incorporated herein by reference: Benzing, David H., *THE BIOLOGY OF THE BROMELIADS,* Mad River Press, Inc., Eureka (1980); Zimmer, Karl, *BROMELIEN,* Verlag Paul Parey, Berlin (1986); and Rauh, Werner, *BROMELIEN,* Verlag Eugen Ulmer, Stuttgart (1981).

The new cultivar was selected from the progeny of a cross made by Elly Bak and Nicolaas D. M. Steur in Assendelft, The Netherlands, in 1993. The female or seed parent was *Aechmea fasciata* Code No. 95265271, and the male or pollen parent was *Aechmea fasciata* Code No. 95265026.

The new cultivar was discovered by the inventors from the progeny of the above cross stated in 1995 in Assendelft, The Netherlands. The new variety 'Primera' was recognized for its spineless, dark greyed-green leaves with transverse white bands and patches. Horticultural evaluation by the inventors of subsequent generations of propagation by offshoots carried out under the direction of the inventors in Assendelft, The Netherlands, has clearly demonstrated that the combination of characteristics as disclosed herein for the new cultivar 'Primera' are firmly fixed and are retained through successive generations of asexual reproduction.

'Primera' has not been tested under all available environmental conditions. The phenotype may vary with variations in environmental conditions, such as temperature, light intensity, frequency of fertilization, composition of fertilizer, day length and humidity, with, however, any change in the genotype of the new cultivar.

The following traits have been repeatedly observed to be characteristics which, in combination, distinguish *Aechmea fasciata* 'Primera' from the closest comparison cultivar, *Aechmea fasciata* 'Morgana' (unpatented):

'Primera' produces spineless leaves;

Leaves that are dark greyed-green (RHS 189A) with whitish scales and a plant habit which is funnel-formed and rosette in shape.

The color photographic drawing shows typical characteristics of 'Primera', with colors being as true as possible with illustrations of this type. Sheet 1 is a side view of a typical 'Primera' plant. The following description is based on the plant depicted in Sheet 1. The plant was grown in Assendelft, The Netherlands, under the supervision of the inventors in greenhouse conditions typical of the industry.

Color references are made to The Royal Horticultural Society (R.H.S.) Colour Chart.

I. Plant:

*Form/growth habit.*—Stemless, funnel-form rosette.

*Height.*—Approx. 50 cm including inflorescence.

*Diameter.*—Approx. 50 cm.

II. Foliage:

*Size of leaf.*—Length approx. 40–50 cm.

*Width.*—Approximately 8–14 cm.

*Shape of leaf.*—Truncate with spine end, not narrowed at base, arching to slightly recurving.

*Leaf sheaf.*—Ample, slightly contracted into the blade, broadly obovate, not inflated, 12–14 cm wide.

*Color.*—Dark greyed-green (RHS 189A) with transverse white bands and patches RHS 202D.

*Color of upper surface.*—RHS 189A.

*Color of lower surface.*—RHS 189A.

*Avg. no. of leaves.*—Plant which is 50 cm high produces approx. 18 leaves.

*Spines.*—None.

*Leaf margin.*—Without spines.

*Leaf texture.*—Soft-coriaceous.

*Leaf channeling.*—Nearly flat to channeled towards the base.

*Leaf apex shape.*—Truncate with spine end.

III. Inflorescence:

*A. Bracts.*—Primary Bracts. Tip shape: Lanceolate. Texture: Thin, coriaceous.

*Length.*—Approx. 12 cm.

*Width.*—Approx. 2.5 cm.

*Number.*—Approx. 40.

*General shape.*—Lanceolate.

*Margin.*—Entire.

*Color.*—Primary bracts RHS 66D.

*Organization.*—Fasciculately compound, polystichously arranged; very dense, fertile part of the inflorescence of the Primera including the floral bracts, approx. 10 cm long and excluding involucral bracts approx. 12 cm wide; rachis hidden and much reduced.

SCAPE BRACTS

Shape: Sub-erect and re-curving forming a rosette over 25 cm in diameter.

FLORAL BRACTS

Shape: Sub-erect and very densely imbricate, broadly ovate to ovate, entire.

*B. Flowers.*—Flowers sessile, receptacle short and flat; sepals strongly asymmetric with wing extending on left side apex; incurved toward apex approx. 1.2 cm long and 1 cm wide. Petals are free from each other, approx. 3.0 cm long and 0.6 cm wide; ligules on petals (claw) present, 3 cm high; 3 petals per flower. Exposed parts of petals violet-blue (RHS 98A) at margins (fading to purplish-red) and lighter toward center with hidden part white. Sepals are approximately 1.2 cm high, 3 sepals per flower, color is white and tinged with pink at the apex. Anthers dorsifixed, nearly at the middle, linear-sagittate, approx. 6.5 mm long, 6 per flower; white. Stigmas lobed clasping in a spiral. Stamens slightly exceeding the pistil with half of the anthers included. Ovary inferior, approx. 4 mm long. Filaments slightly flattened toward base, unequal but the outer whorl strongly curved (S-shaped) at base; anthers on one level approx. 1.8–2 cm long and inner whorl shortly adnate to the petals; white. Time of blooming In mature plants, a fully grown plant can produce an inflorescence containing approximately 150 flowers and can bloom anytime throughout the year starting approximately 11 weeks after natural induction or induction by treatment of acetylene. Duration of blooms Each flower blooms 1 day, and the total length of blooming of the whole inflorescence is 4 weeks.

*C. Seed characteristics.*—Sterile hybrid and therefore no fruit or seed produced.

*D. Disease and pest resistance.*—There is no known information.

We claim:

1. A new and distinct cultivar of *Aechmea fasciata* named 'Primera' as illustrated and described.

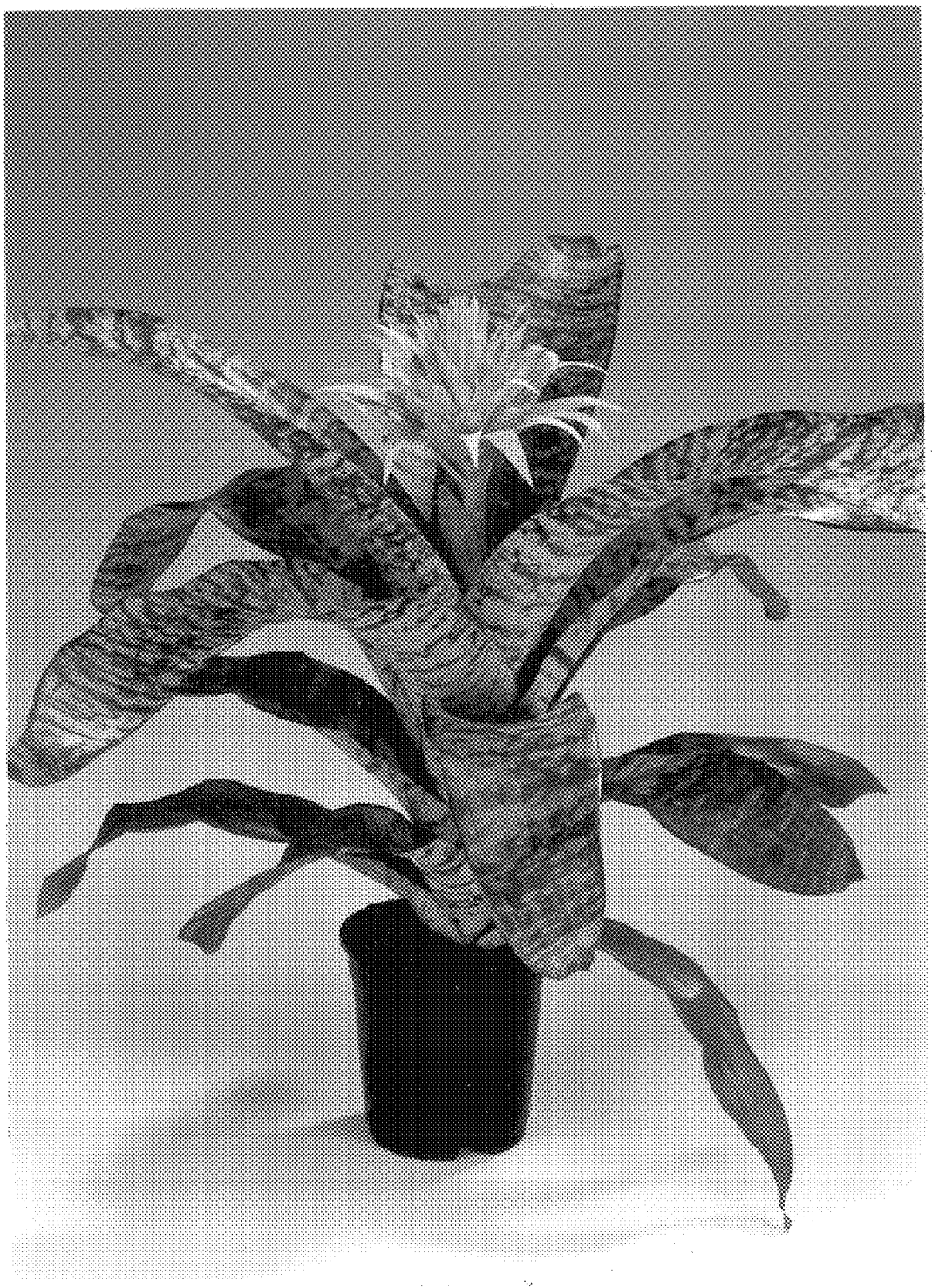

* * * * *